United States Patent [19]
Denzel et al.

[11] 3,965,108
[45] June 22, 1976

[54] AMINO DERIVATIVES OF [1,2,3]THIADIAZOLO[5,4-b] PYRIDINE-6-CARBOXYLIC ACIDS AND ESTERS

[75] Inventors: Theodore Denzel, Regensburg; Hans Hoehn, Tegernheim, both of Germany

[73] Assignee: E. R. Squibb & Sons, Inc., Princeton, N.J.

[22] Filed: May 12, 1975

[21] Appl. No.: 576,418

[52] U.S. Cl. .................. 260/294.8 C; 260/295.5 R; 260/294.8 G; 424/266
[51] Int. Cl.² ........................................ C07D 213/55
[58] Field of Search .............................. 260/294.8 C

[56] References Cited
UNITED STATES PATENTS
3,925,388  12/1975  Hoehn et al. ................ 260/294.8 C

*Primary Examiner*—Alan L. Rotman
*Attorney, Agent, or Firm*—Lawrence S. Levinson; Merle J. Smith

[57] ABSTRACT

New derivatives of [1,2,3]thiadiazolo[5,4-b]pyridin-6-carboxylic acids, esters and their acid addition salts have the general formula

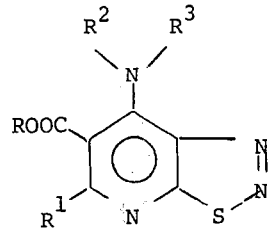

They are useful as central nervous system depressants and antiinflammatory agents.

12 Claims, No Drawings

AMINO DERIVATIVES OF (1,2,3)THIADIAZOLO(5,4-B) PYRIDINE-6-CARBOXYLIC ACIDS AND ESTERS

SUMMARY OF THE INVENTION

The invention relates to new amino derivatives of [1,2,3]thiadiazolo [5,4-b]pyridine-6-carboxylic acids and esters and acid addition salts thereof, having the general formula

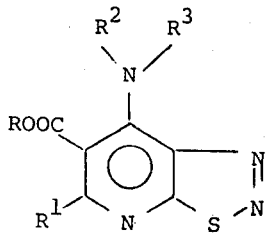

(I)

The symbols have the following meaning in formula I and throughout this specification:

R and $R_1$ each is hydrogen or lower alkyl.

The basic nitrogen group

is an acylic amino moiety, wherein $R^2$ and $R^3$ each is hydrogen, lower alkyl, lower alkanoyl, phenyl, substituted phenyl or di(lower alkyl-amino)-lower alkyl.

The lower alkyl groups in any of the foregoing radicals include straight or branched chain $C_1$ to $C_7$ hydrocarbon groups. Examples are methyl, ethyl, propyl, isopropyl etc. Lower alkyl groups of 1 to 4 carbon atoms are preferred especially the 1 and 2 carbon members of this group.

The substituted phenyl groups include one or two simple substituents ($R^4$), prefereably only one substituent, but they are the same groups if disubstituted, i.e., lower alkyl, lower alkoxy, halogen (fluorine, chlorine, bromine or iodine, preferably chlorine or bromine), trifluoromethyl, amino or caboxy). Examples of the types of groups contemplated are o-, m- or p-chlorophenyl, o-, m- or p-tolyl, 2,5-dichlorophenyl, 3-trifluoromethylphenyl, etc.

The lower alkanoyl groups are the acyl radicals of the lower fatty acids ($C_2$ to $C_7$) e.g., acetyl, propionyl, butyryl, etc., preferably the first two.

The lower alkoxy groups are $C_1$ to $C_7$ groups like methoxy, ethoxy, propoxy, isopropoxy, butoxy, etc., especially the first two.

Preferred embodiments of this invention are as follows:

R is hydrogen or lower alkyl of 1 to 4 carbon atoms, especially ethyl.

$R^1$ is hydrogen or lower alkyl of 1 to 4 carbon atoms, especially methyl.

$R^2$ $R^3$ each is hydrogen, lower alkyl of 1 to 4 carbon atoms, especially butyl.

DETAILED DESCRIPTION

The new compounds of formula I are formed by the following series of reactions.

A 4,6-dihydroxypyridine-3-carboxylic acid ester of the formula

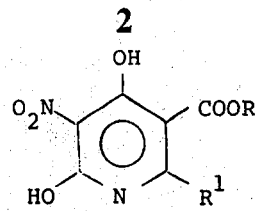

(II)

[produced analogous to the procedure described in Chem. Ber. 99, 244 (1966) ], wherein R is lower alkyl and $R^1$ is the same as above defined, is made to react with an inorganic acid chloride like phosphorus oxychloride producing a compound of the formula

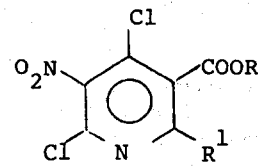

(III)

with two chlorine atoms in the 4-and 6-positions of the molecule. This compound is now treated with an amine of the formula

(IV)

in the presence of a base, e.g., an alkylamine like triethylamine, forming a compound of the formula

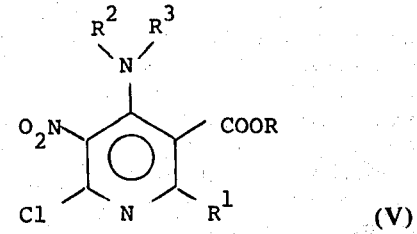

(V)

Reaction of the compound of formula V with an alkali metal sulfide like sodium sulfide, produces a compound of the formula

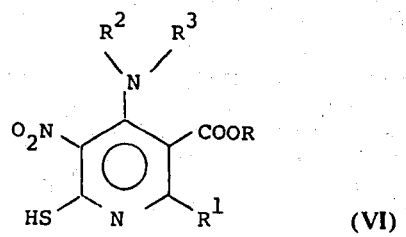

(VI)

with a mercapto group in the 6-position. This compound is then reduced by means of a metal-acid pair like zinc or iron in acetic acid.

This reaction results in the formation of a compound of the formula

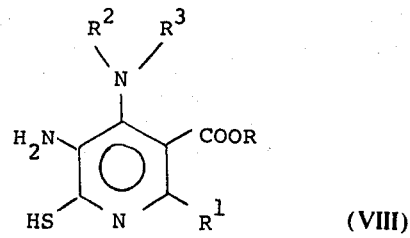

(VIII)

Compounds of formula I are now produced by nitrosation of the compound of formula VII, e.g., with an alkali metal nitrite such as sodium nitrite in an acid medium like acetic acid.

The esters are converted to the acid, i.e., wherein R is hydrogen, with a dilute alkali metal hydroxide like sodium hydroxide.

The compounds of formula I form salts which are also part of this invention. The salts include acid addition salts, particularly the non-toxic, physiologically acceptable members. The bases of formula I form salts by reaction with a variety of inorganic acid organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating the product, e.g., by forming and precipitating a salt (which is not necessarily physiologically acceptable) in an appropriate medium in which the salt is insoluble, then after separation of the salt, neutralizing with a base such as barium hydroxide or sodium hydroxide, to obtain the free base of formula I. Other salts can then be formed from the free base by reaction with an equivalent of acid.

The new compounds of this invention are central nervous system depressants and are useful as tranquilizers or ataractic agents for the relief of anxiety and tension states, for example, in mice, cats, rats, dogs and other mammalian species, in the same manner as chlordiazepoxide. For this purpose a compound or mixture of compounds of formula I, or non-toxic, physiologically acceptable acid addition salt thereof is administered orally or parenterally in a conventional dosage form such as tablet, capsule, injectable or the like. A single dose, or preferably 2 to 4 divided daily doses, provided on a basis of about 3 to 50 mg. per kilogram per day, preferably about 3 to 15 mg. per kilogram per day, is used. These are conventionally formulated in an oral or parenteral dosage form such as those mentioned above by compounding about 10 to 250 mg. per unit of dosage with conventional vehicle, excipient, binder, preservative, stabilizer, flavor or the like as called for by accepted pharmaceutical practice.

The new compounds of this invention, in addition, have antiinflammatory properties and are useful, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay in rats. The active substance can be utilized in compositions such as tablets, capsules, solutions or suspensions containing up to about 300 mg. per unit of dosage of a compound or mixture of compounds of formula I or physiologically acceptable acid addition salt thereof. These are compounded in conventional manner with a physiologically acceptable vehicle or carrier, excipient, binder, preservative, stabilizer, flavor, etc. as called for by accepted pharmaceutical practice. Topical preparations containing about 0.03 to 3 percent by weight of active substance in a lotion or cream are also useful.

The following examples constitute especially preferred embpodiments and also illustrate how these and other members of this group are produced. Simple variation of the reactants and substitution in the reaction sequences described below, readily yield other compounds within the scope of the invention. All temperatures are in centigrade degreees.

EXAMPLE 1

7-(Butylamino)-5-methyl [1,2,3]thiadiazolo [5,4-b]pyridine-6-carboxylic acid, ethyl ester a. 4,6-dichloro-2-methyl-5-nitropyridine-3-carboxylic acid, ethyl ester 242 g. of 4,6-dihydroxy-2-methyl-5-nitropyridine-3-carboxylic acid, ethyl ester (1 mol.) are heated at 80° with 500 ml. of phosphorus oxychloride for 60 hours. After this time, the excess phosphorus oxychloride is removed in vacuo and the black residue is decomposed by pouring into ice water. The precipitate is filtered off and recrystallized from petroleum ether using charcoal to obtain 4,6-dichloro-2-methyl-5-nitropyridine-3-carboxylic acid, ethyl ester, yield 195 g. (70%); m.p. 45°–46°.

b. 4-butylamino-6-chloro-2-methyl5-nitropyridine-3-carboxylic acid, ethyl ester 139.5 g. of 4,6-dichloro-2-methyl-5-nitropyridine-3-carboxylic acid, ethyl ester (0.5 mol.) are dissolved in about 500 ml. of methanol. 60 g. of triethylamine are added and the solution is heated at reflux temperature. At this point, 36.5 g. n-butylamine are added dropwise. After the addition is completed, the heating is continued for 10 minutes. The solvent is then removed in vacuo and 500 ml. of ethyl acetate are added to the residue. The triethylamine hydrochloride is filtered off and the solvent evaporated. The resulting yellow oil, 4-butylamino-6-chloro -2methyl-5nitropyridine-3-carboxylic acid, ethyl ester is crystallized with 300 ml. of methanol, yield 110 g. (70%); m.p. 33°–35° (methanol).

c. 4-butylamino-6-mercapto-2-methyl-5-nitropyridine-3-cabroxylic acid, ethyl ester 31.5 g. of 4-butylamino-6-chloro-2-methyl-5-nitropyridine-3-carboxylic acid, ethyl ester (0.1 mol.) are dissolved in 100 ml. of alcohol. 14.8 g. of sodium sulfide monohydrate and about 2 ml. of water are added. The mixture is stirred for 1 hour without cooling. the precipitated 4-butylamino-6-mercapto-2-methyl-5-nitropyridine-3carboxylic acid, ethyl ester is filtered off, yield 27.5 g. (88%); m.p. 140°–142° (ethanol).

d. 5-amino-4-butylamino-6-mercapto-2-methylpyridine-3-carboxylic acid, ethyl ester 6.2 g. of 4-butylamino-6-mercapto-2-methyl-5-nitropyridine-3-carboxylic acid, ethyl ester (0.02 mol.) are dissolved in 25 ml. of acetic acid at reflux temperature with stirring. Zinc dust is added cautiously in small portions until the solvent is colorless. The inorganic preceipitate is then filtered off, the solvent removed and the residue dissolved in 10 ml. of methanol. The product, 5-amino-4-butylamino-6-mercapto-2-methylpyridine-3-carboxylic acid, ethyl ester, precipitates after the addition of aqueous ammonia, yield 3.6 g. (64%); m.p. 103°–105° (ethyl acetate).

e. 7-(butylamino)-5-methyl[1,2,3]thiadiazolo [5,4-b]pyridine-6-carboxylic acid, ethyl ester 2.8 g. of 5-amino-4-butylamino-6-mercapto-2-methyl-pryridine -3-carboxylic acid, ethyl ester are dissolved in 10 ml. of acetic acid. The solution is cooled to about 10°, then 1 g. of sodium nitrite in 3 ml. of water are dropped in and the mixture is stirred room temperature for 10 hours. After this time, the insoluble products are filtered off and the filtrate is evaporated to dryness. The residue is recrystallized from diethyl ether and yields 2.2 g. of 7-butylamino-5-methyl [1,2,3]thiodiazolo[5,4-b]pyridine-6-carboxylic acid, ethyl ester (75%); m.p. 57°–58°.

EXAMPLE 2

7-[[(3-Dimethylamino) propyl]amino]-5-methyl [1,2,3]thiadiazolo [5,4-b]pyridine -6-carboxylic acid ethyl ester a. 4-[[(3-dimethylamino) propyl]amino]-6-chloro-2-methyl-5nitropyridine3-carboxylic acid, ethyl ester 139 g. of 4,6-dichloro-2-methyl-5-nitropyridine-3-carboxylic acid, ethyl ester (0.5 mol.) are dissolved in about 500 ml. of methanol. 60 g. of triethylamine are added and the solution is heated at reflux temperature. At this point, 50.1 g. of 3-(dimethylamino) propylamine are added dropwise. After the addition is completed, heating is continued for 10 minutes. The solvent is removed in vacuo and the residue is suspended in 200 ml. of water. The aqueous mixture is made alkaline with 10% sodium hydroxide solution and extracted three times with 200 ml. portions of ethyl acetate. The organic layer is dried over calcium chloride, evaporated to dryness and crystallized with petroleum ether to obtain 4-[[(3-dimethylamino)propyl]-amino]-6-chloro-2-methyl-5-nitropyridine-3-carboxylic acid, ethyl ester, yield 102 g. (59%); m.p. 20°.

b. 4-[[(3-dimethylamino) propyl]amino]-6-mercapto-2-methyl-5-nitropyridine-3-carboxylic acid, ethyl ester 34.5 g. of 4-[[(3-dimethylamino) propyl]amino]-6-chloro-2-methyl-5-nitropyridine-3-carboxylic acid, ethyl ester are dissolved in 100 ml. of ethanol. 15 g. of sodium sulfide in 10 ml. of water are added and the mixture is stirred without cooling for 1 hour. After this time, the precipitated 4-[[(3-dimethylamino)propyl]amino]-6-mercapto-2-methyl-5-nitropyridine-3-carboxylic acid, ethyl ester is filtered off and recrystallized from methanol, yield 18 g. (53%); m.p. 131°–132°.

c. 5-Amino-4-[[(3-dimethylamino)propyl]amino]-6-mercapto-2-methylpyridine-3-carboxylic acid, ethyl ester 6.8 g. of 4-[[(3-dimethylamino)propyl]amino]-6-mercapto-2-methylpyridine-3-carboxylic acid, ethyl ester are dissolved in 50 ml. of acetic acid and held at reflux temperature. Zinc is added until the solution is colorless. The inorganic precipitate is filtered off, the solvent removed and the residue is dissolved in about 10 ml. of methanol. The 5-amino-4-[[(3-dimethylamino)propyl]amino]-6-mercapto-2-methylpyridine-3-carboxylic acid, ethyl ester crystallizes on addition of aqueous ammonia, yield 4.1 g. (66%); m.p. 110°–112° (ethyl acetate).

d. 7-[[(3-dimethylamino]propyl]amino-5-methyl[1,2,3]thiadiazolo[5,4-b]pyridine-6-carboxylic acid, ethyl ester 3.1 g. of 5-amino-4-[[(3-dimethylamino)propyl]amino]-6-mercapto-2-methylpyridine-3-carboxylic acid, ethyl ester are treated with sodium nitrite and acetic acid as described in Example 1 e to obtain 7-[[(3-dimethylamino)propyl]amino]-5-methyl[1,2,3]-thiadiazolo[5,4-b]pyridine-6-carboxylic acid, ethyl ester, yield 68%; m.p. < 15° (ether).

EXAMPLE 3

7-(sec.Butylamino)-5-methyl[1,2,3]thiadiazolo[5,4-b]pyridine-6-carboxylic acid, ethyl ester a. 4-sec. butylamino-6-chloro-2-methyl-5-nitropyridine-3-carboxylic acid, ethyl ester By substituting sec. butylamine for n-butylamine in the procedure of Example 1 b, 4-(sec. butylamino)-6-chloro-2-methyl-5-nitropyridine-3-carboxylic acid, ethyl ester is obtained, yield 68%; m.p. 31°–32° (methanol).

b. 4-sec. butylamino-6-mercapto-2-methyl-5-nitropyridine-3-carboxylic acid, ethyl ester By substituting 4-sec. butylamino-6-chloro-2-methyl-5-nitropyridine-3-carboxylic acid, ethyl ester for 4-butylamino-6-chloro-2-methyl-5-nitropyridine-3-carboxylic acid, ethyl ester in the procedure of Example 1 c, 4-sec. butylamino-6-mercapto-2-methyl-5-nitropyridine-3-carboxylic acid, ethyl ester is obtained, yield 82%; m.p. 156°–157° (methanol).

c. 5-amino-4-sec.butylamino-6-mercapto-2-methylpyridine-3-carboxylic acid, ethyl ester 6.2 g. of 4-sec.butylamino-6-mercapto-2-methyl-5-nitropyridine-3-carboxylic acid, ethyl ester are dissolved in 50 ml. of acetic acid. Iron dust is added carefully at reflux temperature until the mixture is colorless. The excess of iron is filtered off and the filtrate is evaporated to dryness. The oily residue is dissolved in 10 ml. of methanol and precipitated by the addition of aqueous ammonia to obtain 5-amino-4-sec.butylamino-6-mercapto-2-methylpyridine-3-carboxylic acid, ethyl ester, yield 3 g. (53%); m.p. 88°–89° (ethyl acetate).

d. 7-(sec.butylamino)-5-methyl[1,2,3]thiadiazolo[5,4-b]-pyridine-6-carboxylic acid, ethyl ester By treating 5-amino-4-sec.butylamino-6-mercapto-2-methylpyridine-3-carboxylic acid, ethyl ester with sodium nitrite in acetic acid as described in Example 1 e, 7-(sec.-butylamino)-5-methyl[1,2,3]thiadiazolo[5,4-b]pyridine-6-carboxylic acid, ethyl ester is obtained, yield 72% m.p. 48°–50° (ether).

EXAMPLE 4

7-Ethylamino-5-methyl[1,2,3]thiadiazolo[5,4-b]pyridine-6-carboxylic acid, ethyl ester 4,6-Dichloro-2-methyl-5-nitropyridine-3-carboxylic acid, ethyl ester is treated with ethylamine according to the procedure in Example 1 b, and this product is processed as described in Example 1 parts c to e to obtain 7-ethylamino-5-methyl[1,2,3]thiadiazolo[5,4-b]pyridine-6-carboxylic acid, ethyl ester, m.p. 85°–87° (ether).

EXAMPLE 5

7-(Isopropylamino)-5-methyl[1,2,3]thiadiazolo[5,4-b]pyridine-6-carboxylic acid, ethyl ester 4,6-Dichloro-2-methyl-5-nitropyridine-3-carboxylic acid, ethyl ester is treated with isopropylamine according to the procedure of Example 1, parts b to e. 7-(isopropylamino)-5-methyl[1,2,3]thiadiazolo[5,4-b]pyridine-6-carboxylic acid, ethyl ester is obtained, m.p. 62°–65° (ether).

Treatment of the above product with sodium hydroxide yields 7-(isopropylamino)-5-methyl[1,2,3]-thiadiazolo[5,4-b]-pyridine-6-carboxylic acid. Addition of 2N hydrochloric acid in ethanol yields the hydrochloride salt.

The following additional compounds are obtained by the procedure of Example 1 by substituting the appropriate amine for the n-butylamine and for the 4,6-dichloro-2-methyl-5-nitropyridine-3-carboxylic acid the appropriately substituted analog:

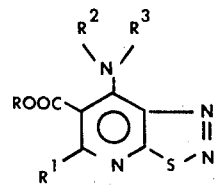

| Example | R² | R³ | R¹ | R |
|---|---|---|---|---|
| 6 | CH₃—CH₂ | CH₃—CH₂ | CH₃ | C₂H₅ |
| 7 | —(CH₂)₃N(C₂H₅)₂ | H | CH₃ | C₂H₅ |
| 8 | CH₃—CH₂ | CH₃—CH₂ | CH₃—CH₂ | C₂H₅ |
| 9 | —(CH₂)₂N(C₂H₅)₂ | H | H | C₂H₅ |
| 10 | H | H | CH₃ | C₂H₅ |
| 11 | C₃H₇ | C₃H₇ | CH₃ | C₂H₅ |
| 12 | H | H | H | H |
| 13 | —(CH₂)₃CH₃ | H | H | CH₃ |
| 14 | —(CH₂)₃CH₃ | H | H | H |
| 15 | —(CH₂)₃CH₃ | H | C₃H₇ | C₂H₅ |
| 16 | 3-CF₃-C₆H₄— | H | CH₃ | C₂H₅ |
| 17 | 3-CF₃-C₆H₄— | H | H | H |
| 18 | —CH₂—CH(CH₃)₂ | H | H | C₂H₅·HBr |
| 19 | —CH(CH₃)(CH₂—CH₃) | H | H | C₃H₇ |
| 20 | 2,6-Cl₂-C₆H₃— | H | H | C₂H₅ |
| 21 | 4-CH₃O-C₆H₄— | H | H | C₂H₅ |
| 22 | 4-CH₃-C₆H₄— | H | CH₃ | C₂H₅ |
| 23 | 2-Br-C₆H₄— | H | H | CH₃ |
| 24 | —CH₂N(CH₃)₂ | H | H | H·HCl |
| 25 | —COCH₃ | H | H | C₂H₅ |
| 26 | —COCH₃ | —COCH₃ | CH₃ | H |
| 27 | C₆H₅— | H | H | C₂H₅ |
| 28 | —COC₂H₅ | H | H | C₂H₅ |
| 29 | 2,3-(CH₃)₂-C₆H₃— | H | H | C₂H₅ |
| 30 | 2,6-(CH₃)₂-C₆H₃— | H | CH₃ | H |
| 31 | 2-COOH-C₆H₄— | H | H | C₂H₅ |

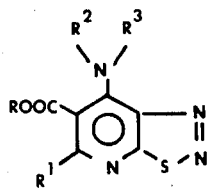

| Example | $R^2$ | $R^3$ | $R^1$ | R |
|---|---|---|---|---|
| 32 | 3,4-di(CH$_3$O)-C$_6$H$_3$- | H | CH$_3$ | C$_2$H$_5$ |
| 33 | 4-NH$_2$-C$_6$H$_4$- | H | H | C$_2$H$_5$ |
| 34 | | H | CH$_3$ | C$_2$H$_5$ |
| 35 | CH$_3$ | CH$_3$ | CH$_3$ | C$_4$H$_9$ |
| 36 | CH$_3$ | H | H | H |
| 37 | 2-NH$_2$-C$_6$H$_4$- | H | H | C$_2$H$_5$ |

What is claimed is:

1. A compound of the formula

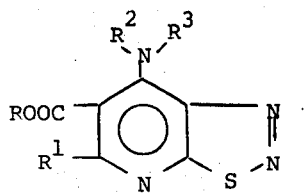

wherein R and $R^1$ each is hydrogen or lower alkyl; and $R^2$ and $R^3$ each is hydrogen, lower alkyl or di (lower alkylamino)lower alkyl;
and physiologically acceptable acid addition salts thereof.

2. A compound as in claim 1 wherein R, $R^1$, $R^2$ and $R^3$ each is hydrogen or C$_1$-C$_4$ lower alkyl.

3. A compound as in claim 1 wherein $R^3$ is hydrogen.

4. A compound as in claim 3 wherein $R^2$ is lower alkyl.

5. A compound as in claim 1 wherein R, $R^1$ and $R^2$ each is lower alkyl and $R^3$ is hydrogen.

6. A compound as in claim 1 wherein R and $R^1$ each is lower alkyl, $R^2$ is di-(lower alkylamino)-lower alkyl and $R^3$ is hydrogen.

7. A compound as in claim 1 wherein R is ethyl, $R^1$ is methyl, $R^2$ is butyl and $R^3$ is hydrogen.

8. A compound as in claim 7 wherein the butyl group is n-butyl.

9. A compound as in claim 7 wherin the butyl group is sec.butyl.

10. A compound as in claim 1 wherein R is ethyl, $R^1$ is methyl, $R^2$ is isopropyl and $R^3$ is hydrogen.

11. A compound as in claim 1 wherein the R an $R^2$ each is ethyl, $R^1$ is methyl and $R^3$ is hydrogen.

12. A compound as in claim 1 wherein R is ethyl, $R^1$ is methyl, $R^2$ is 3-(dimethylamino)propyl and $R^3$ is hydrogen.

* * * * *

UNITED STATES PATENT AND TRADEMARK OFFICE
CERTIFICATE OF CORRECTION

PATENT NO. : 3,965,108
DATED : June 22, 1976
INVENTOR(S) : Theodor Denzel et al.

It is certified that error appears in the above-identified patent and that said Letters Patent are hereby corrected as shown below:

Column 1, line 47, delete "caboxy" and add --$_2$carboxy--.
Column 1, line 63, delete "R$^2$R$^3$" and add -- R$^2$ and R$^3$--.

Column 9, Example 33, under R$^2$ the formula should appear as follows:

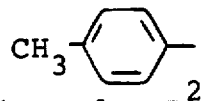

Column 9, Example 34, under R$^2$ the formula should appear as follows:

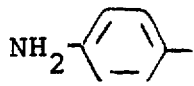

Signed and Sealed this second Day of August 1977

[SEAL]

Attest:

RUTH C. MASON
Attesting Officer

C. MARSHALL DANN
Commissioner of Patents and Trademarks